United States Patent
Vinogradov et al.

(10) Patent No.: US 9,714,922 B2
(45) Date of Patent: Jul. 25, 2017

(54) MAGNETOSTRICTIVE PROBE WITH MECHANICAL AND FLUID COUPLING FOR GUIDED WAVE TESTING OF TUBULAR STRUCTURES

(71) Applicant: Southwest Research Institute, San Antonio, TX (US)

(72) Inventors: Sergey A. Vinogradov, San Antonio, TX (US); Charles E. Duffer, San Antonio, TX (US); Glenn M. Light, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 163 days.

(21) Appl. No.: 14/924,178

(22) Filed: Oct. 27, 2015

(65) Prior Publication Data

US 2017/0115204 A1   Apr. 27, 2017

(51) Int. Cl.
| | | |
|---|---|---|
| G01N 22/04 | (2006.01) | |
| G01N 29/07 | (2006.01) | |
| G01N 29/24 | (2006.01) | |
| G01N 29/44 | (2006.01) | |
| G01N 27/82 | (2006.01) | |

(52) U.S. Cl.
CPC .................... *G01N 27/82* (2013.01)

(58) Field of Classification Search
CPC ......... G01N 29/2412; G01N 2291/044; G01N 2291/2634; G01N 27/82; G01N 29/11; G01N 2291/0422; G01N 2291/0421; G01N 29/265; G01N 2291/0425; G01N 29/043; G01N 29/07; G01N 29/262; G01N 2291/2636; G01F 23/2963; G01F 23/72; G01F 23/68; G01M 5/0025; G01M 5/0066

See application file for complete search history.

(56) References Cited

U.S. PATENT DOCUMENTS

| | | | | |
|---|---|---|---|---|
| 5,848,549 A | * | 12/1998 | Nyce ................. | G01F 23/72 324/207.13 |
| 5,986,449 A | * | 11/1999 | Koski ................. | G01F 23/2963 324/207.13 |
| 6,429,650 B1 | * | 8/2002 | Kwun ................. | G01N 29/11 324/220 |
| 7,019,520 B2 | | 3/2006 | Kwun et al. | |
| 7,474,092 B1 | * | 1/2009 | Kwun ................. | G01N 29/043 324/238 |
| 7,573,261 B1 | * | 8/2009 | Vinogradov ........ | G01N 27/82 324/240 |
| 7,821,258 B2 | | 10/2010 | Vinogradov | |

(Continued)

Primary Examiner — Alesa Allgood
(74) Attorney, Agent, or Firm — Livingston Law Firm

(57) ABSTRACT

A probe for use in magnetostrictive testing of tubular structures. The probe has a handle and an outer tube, the latter having an expandable probe head for insertion into the tubular structure. A pair of magnetostrictive sensors is mounted in or on the probe head. A flexible bladder is located inside the outer tube in the area of the probe head, and communicates with a pressurizing cartridge in the probe handle via a bladder tube. The bladder is operable to expand, causing the probe head to expand, which moves the sensors toward the inner wall of the tubular structure. The probe is also equipped with a couplant injector that delivers coupling fluid to any gaps between the inner surface of the tubular structure and the outer surface of the probe.

17 Claims, 7 Drawing Sheets

(56) References Cited

U.S. PATENT DOCUMENTS

| | | | | |
|---|---|---|---|---|
| 8,978,464 B2* | 3/2015 | Prinstil | ............... | G01F 23/30 |
| | | | | 324/209 |
| 2002/0105324 A1* | 8/2002 | Kwun | ............... | G01N 29/11 |
| | | | | 324/240 |
| 2009/0021253 A1* | 1/2009 | Kwun | ............... | G01N 29/043 |
| | | | | 324/238 |
| 2014/0224010 A1* | 8/2014 | Prinstil | ............... | G01F 23/30 |
| | | | | 73/313 |

* cited by examiner

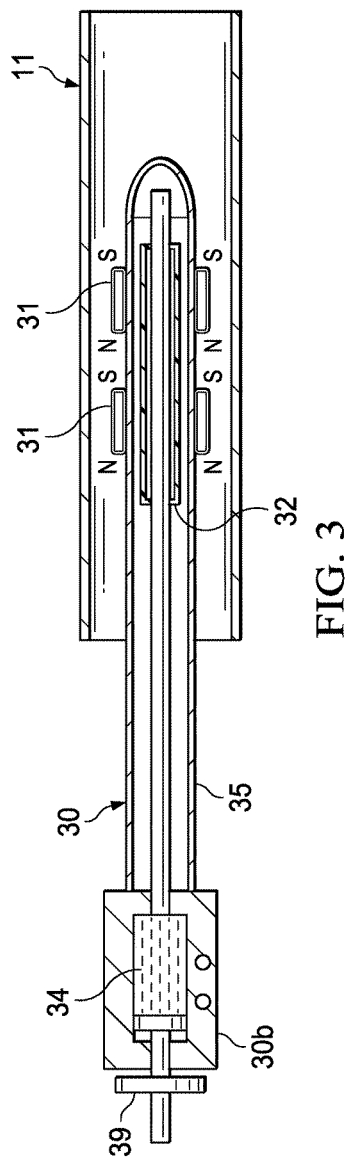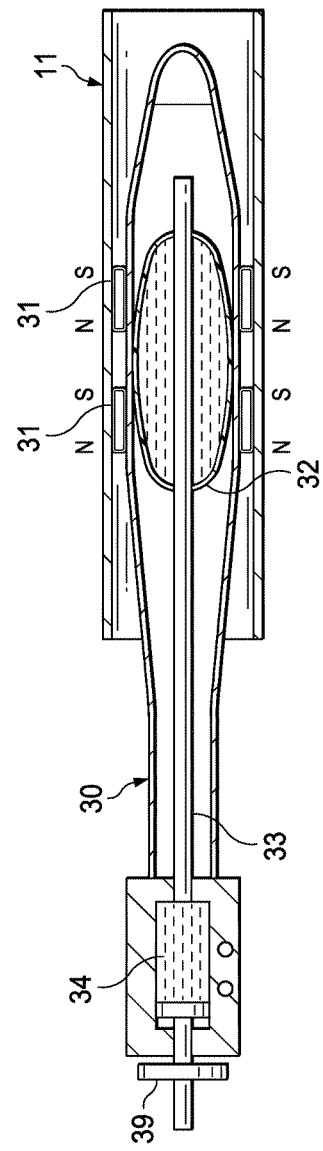

MAGNETOSTRICTIVE PROBE WITH MECHANICAL AND FLUID COUPLING FOR GUIDED WAVE TESTING OF TUBULAR STRUCTURES

TECHNICAL FIELD OF THE INVENTION

This invention relates to nondestructive testing using guided wave testing (GWT) and magnetostrictive sensor (MsS) technology, and more particularly, to a probe used for testing tubular structures.

BACKGROUND OF THE INVENTION

One effective method for inspecting and monitoring various structures is guided wave testing (GWT) using magnetostrictive sensor (MsS) technology. The principle of magnetostriction is based on either shifting or oscillation/rotation between magnetic domains in the material due to applied magnetic fields. Typically, a permanent magnetic field is used to give the domains a preferred orientation. Variable magnetic fields are also applied to initiate the rotation of the domains causing the dimensional changes. Depending on the mutual orientation (in-plane or out-of-plane) and on the mutual magnitude of the magnetic fields, oscillation of domains can produce longitudinal or transverse vibrations.

There are many applications of MsS testing, with testing of pipelines being a common application. Pipeline testing applications often use MsS transducers placed around the outside of the pipeline.

In contrast to testing pipelines, for which access to the inside of the pipeline may be impractical, testing other types of tubular structures may be best performed with an MsS transducer placed inside the tubular structure. For example, testing heat exchanger tubes is often performed using an MsS probe inserted into an open end of the tubing.

If the generated MsS waves are coupled to the inside of the tube, the waves propagate along the tube and are partially reflected by geometric irregularities present in the tube, such as corrosion defects. The reflected signals are then detected by the MsS transducer. From the arrival time of the reflected signal and the signal amplitude, the axial location of the irregularity and its severity are determined.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIGS. 3 and 4 illustrate an MsS probe for use in testing tubular structures, in an unexpanded and expanded mode, respectively.

DETAILED DESCRIPTION OF THE INVENTION

The following description is directed to non destructive testing of tubular structures using MsS transducers (also referred to herein as "sensors"). For purposes of example, this description is in terms of testing heat exchanger tubes. However, it can be easily understood that the same concepts apply to other tubular structures for which access to the inside of the tube can be obtained at one end.

The MsS transducers useful for this application can be those generating torsional and flexural mode guided waves. As described below, the waves are generated in the transducer, and then coupled to the wall by means of mechanical and fluid coupling. Coupling in this manner allows the inspection of tubes of any material (ferromagnetic and non-ferromagnetic).

In general, the testing process begins with inserting an MsS probe into the tube. The probe head carries the MsS sensors, which are then mechanically coupled and fluid-coupled to the inner diameter of the tube. The guided waves are transmitted, their reflections received, and data is collected. Then, the probe is uncoupled and removed.

MsS sensors for testing tubular structures by being placed inside the structure are described in U.S. Pat. No. 7,821,258, entitled "Method and System for Generating and Receiving Torsional Guided Waves in a Structure", to Vinogradov, incorporated by reference herein.

Figure 1:
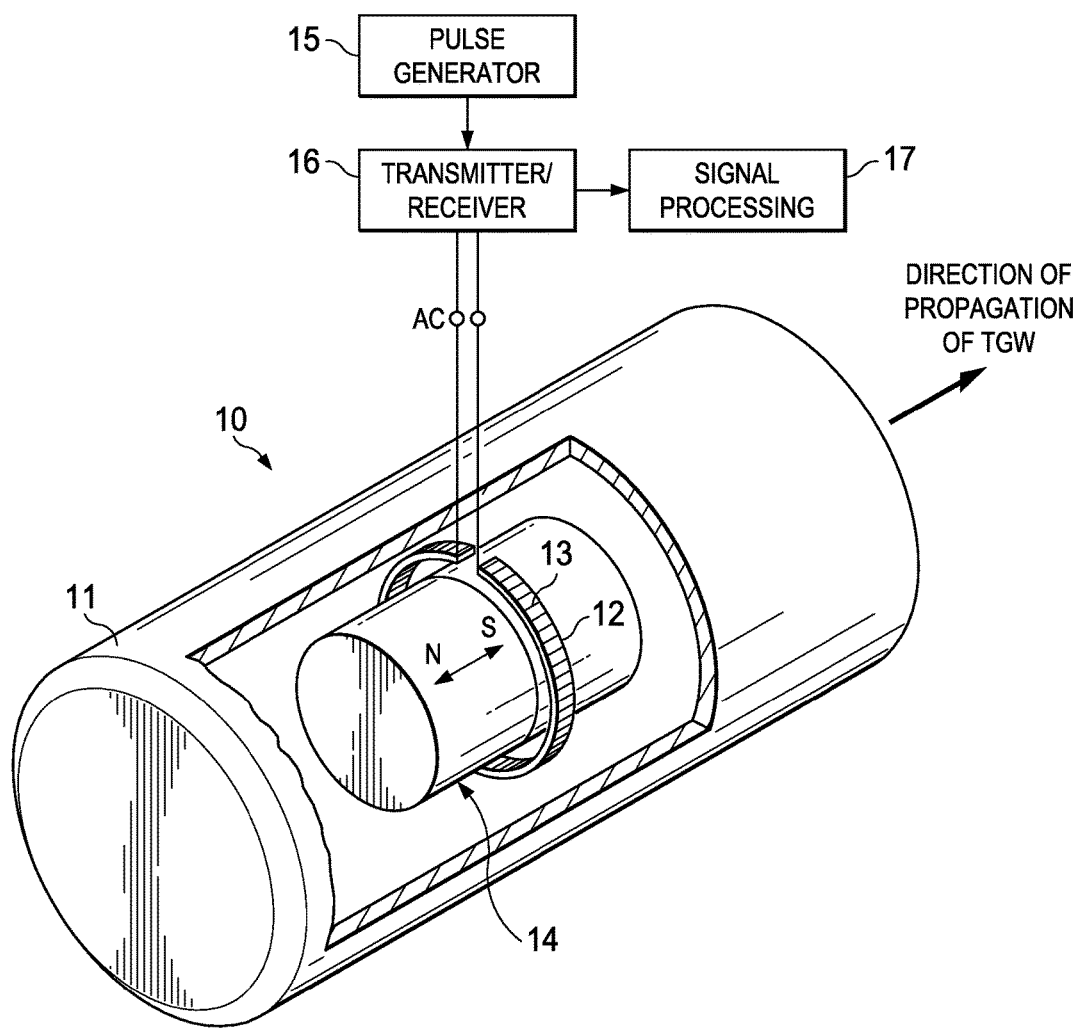
FIG. 1 illustrates the principle of electromagnetic wave generation, using an MsS sensor placed inside a tubular structure.

FIG. 1 illustrates the principle of electromagnetic wave generation, using an MsS sensor 10 placed inside a tubular structure 11. The sensor 10 comprises a ring-shaped magnetostrictive strip 12, with an AC coil 13 wrapped around its short dimension (width). A permanent magnet 14 is located with its poles parallel to the long dimension of the tube. This creates a permanent bias magnetic field in the direction indicated. The AC coil 13 generates an alternating field that is perpendicular to the bias magnetic field.

The direction of the permanent magnetic bias field as well as the orientation of the windings of the AC coil 13 are parallel to the direction of propagation of transversal vibration. The poles of the magnet are located on the sides of the coil to create in-plane magnetization only. This helps to eliminate any longitudinal modes by making domains oscillate in-plane only. When a pulsed alternating current flows through AC coil 13, a torsional guided wave (TGW) propagates in tube 11 in the direction indicated.

In a completed system, with a pulse generator 15 creating an AC pulse that is delivered through transmitter/receiver 16 to AC coil 13, an impulse of alternating current is created in AC coil 13. This impulse of alternating current creates an alternating magnetic bias in magnetostrictive strip 12, which in turn causes the torsional guided waves to propagate in the direction indicated. Of particular importance is that the direction of propagation of the torsional guided waves is the same as the direction of the permanent magnetic field.

If there is a defect in structure 11, a reflected torsional guided wave will be reflected back towards the magnetostrictive strip 12. The magnetostrictive strip 12 will respond with what is known as the inverse Wiedemann effect, which will cause a mechanical impulse in AC coil 13. The reflected torsional guided wave signal detected in AC coil 13 is received by transmitter/receiver 16 and delivered to signal processor 17, which analyzes the signal to locate and estimate the size of the defect.

In variations of this sensor, the permanent magnet 14 can be divided into a series of smaller magnets located along the magnetostrictive strip 12 to ensure that the magnetostrictive strip 12 is fully saturated. Also, the AC coil 13 could be split into a set of coils connected in either parallel or series arrangement for better performance.

Figure 2:
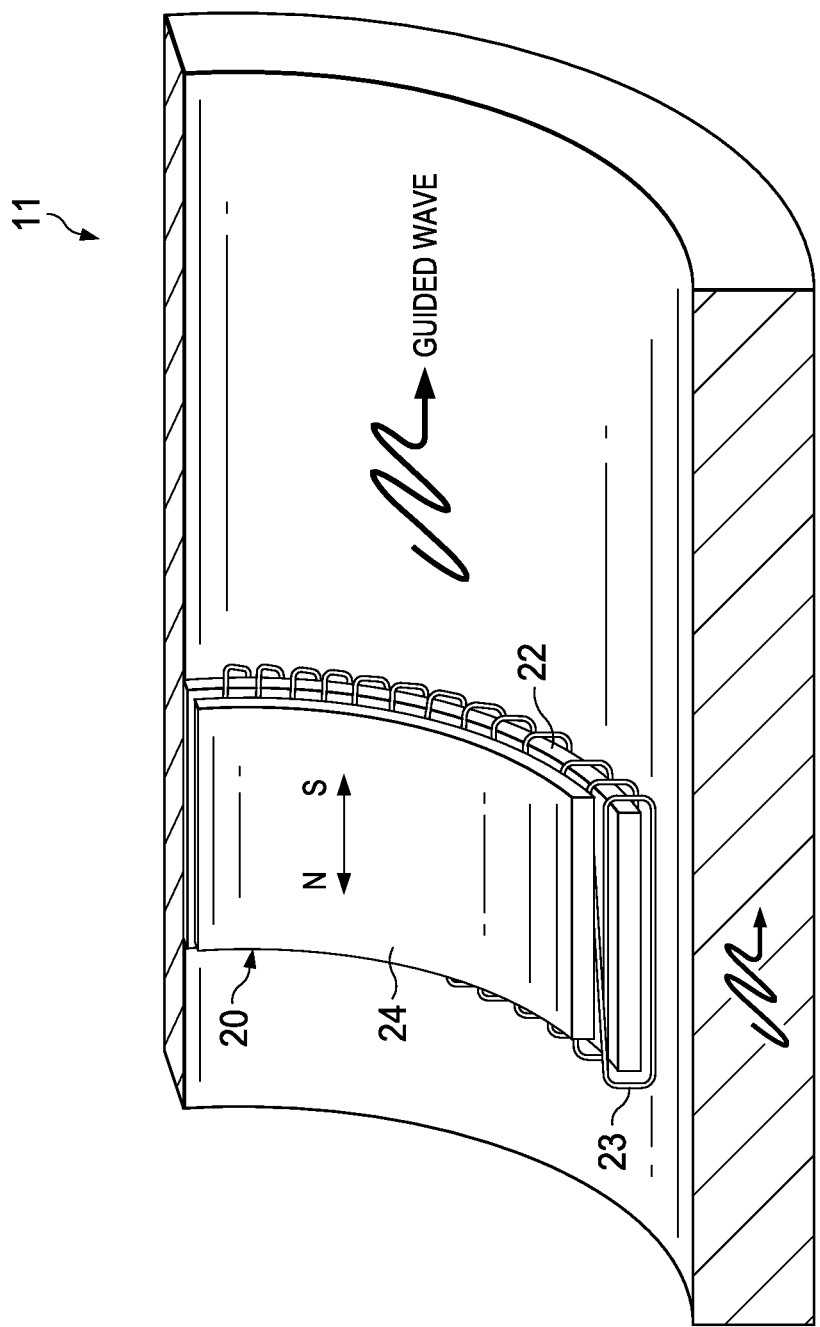
FIG. 2 illustrates a portion of the MsS sensor of FIG. 1, modified for use with the probe of the present invention.

FIG. 2 illustrates a portion of an MsS sensor 20, similar to that of FIG. 1, but adapted for use with the probe of the present invention. In the embodiment of FIG. 2, the permanent magnet 24 is ring-shaped, concentric with and inside of, the ring-shaped ferromagnetic strip 22. The widths (short dimensions) of magnet 24 and strip 22 are approximately the same.

As stated above, magnet 24 is located inside of ferromagnetic strip 22 that has an AC winding 23 around it. With appropriate coupling, magnet 24 magnetically saturates the wall of the tubular structure 11 in the elongated axis direction. The AC winding 23 around strip 22 creates a variable magnetic field in the wall of the tubular structure 11. The AC field, in combination with the permanent magnetic field, generates torsional guided waves that propagate along the elongated axis of the tubular structure 11.

FIGS. 3 and 4 each illustrate an MsS probe 30 for use in testing tubular structures. Probe 30 is typically used at an open end of the tubular structure 11. This allows probe 30 to be inserted a short distance into the tubular structure, and allows an electrical connection to be easily made to the AC windings of its MsS sensors.

Probe 30 uses two MsS sensors 31, both located in a "probe head" area just behind the probe's tip at the insertion end. Each sensor 31 comprises a magnet and a coil wrapped around a ferromagnetic strip. As in FIG. 2, each sensor 31 has its magnet and coil-wrapped strip configured as concentric rings, with the magnet being the inner ring.

Sensors 31 are separated axially by a distance of 0.25 wavelength. The use of two sensors 31 provides improved control over the direction of propagation of guided waves.

FIGS. 3 and 4 illustrate probe 30 in its unexpanded and expanded modes, respectively. As explained below, the probe head portion of probe 30 expands so that its sensors 31 couple to the inner wall of the tube 11. This is accomplished by pressurizing an expandable bladder 32, which causes a flexible outer surface of the probe head to expand.

Bladder 32 is mounted at one end of a bladder tube 33. Bladder tube 33 is in fluid communication with a pressurizing cylinder 34 at its other end, which is at the handle 30*b* of probe 30. Cylinder 34 stores a pressurizing fluid, which may be pneumatic or hydraulic. The pressurizing cylinder 34 delivers the pressurizing fluid to bladder 32 via inner tube 33 when bladder 32 is desired to be pressurized.

An outer tube 35 encloses bladder 32 and bladder tube 33. Outer tube 35 is made from flexible material, at least at the probe head, where it surrounds bladder 32. Thus, when bladder 32 expands, outer tube 35 also expands radially. Alternatively, outer tube 35 could be made to be "flexible" by being split longitudinally or otherwise segmented, in a manner that allows it to expand radially.

Sensors 31 are mounted on the outer surface of outer tube 35 in the area over bladder 32. Thus, when outer tube 35 expands, sensors 31 are moved toward and coupled to the inner wall of tube 11.

While in the unexpanded mode of FIG. 3, the probe 30 is inserted about 1-3 feet deep in the tube. For testing a typical heat exchanger, this places the probe head past the tube sheet, which is a face plate that positions the heat exchanger tubes. The insertion of probe 30 carries sensors 31 into whichever tube is being tested.

In the expanded mode of FIG. 4, the pressurizing cylinder 34 is activated, which causes pressurizing fluid to travel the length of bladder tube 33 and into bladder 32, which then expands. The sensors 31 are moved toward and pressed against the inner wall of tube 11 by the pressurized condition of bladder 32 and outer tube 35.

Various means can be used for activating cartridge 34. In the example of FIGS. 3 and 4, a pressurizing wheel 39 is manually rotated.

Because the sensors 31 have two different radiuses at contracted and expanded positions of the probe, each sensor 31 should have some flexibility in its radial dimension.

Figure 5:
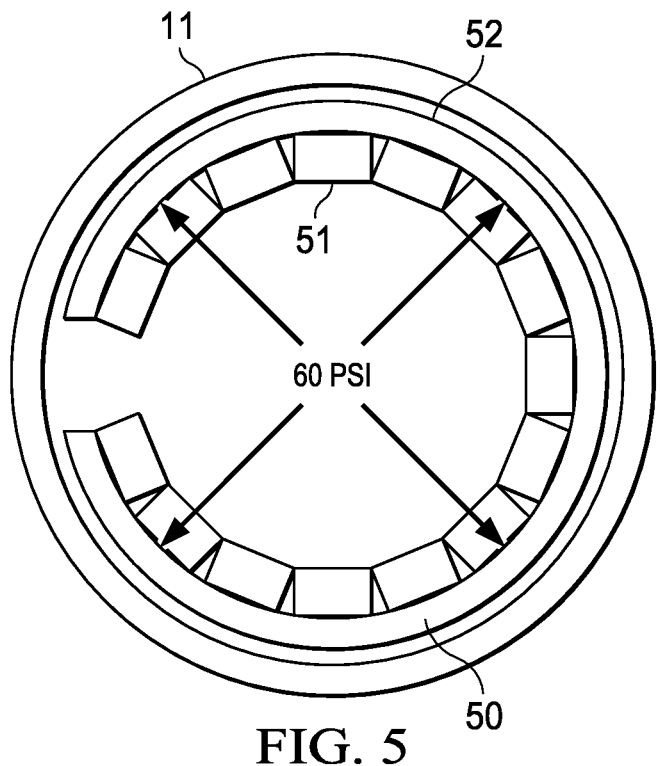
FIGS. 5 and 6 illustrate two sensor configurations that have the ability to expand and contract.
Figure 6:
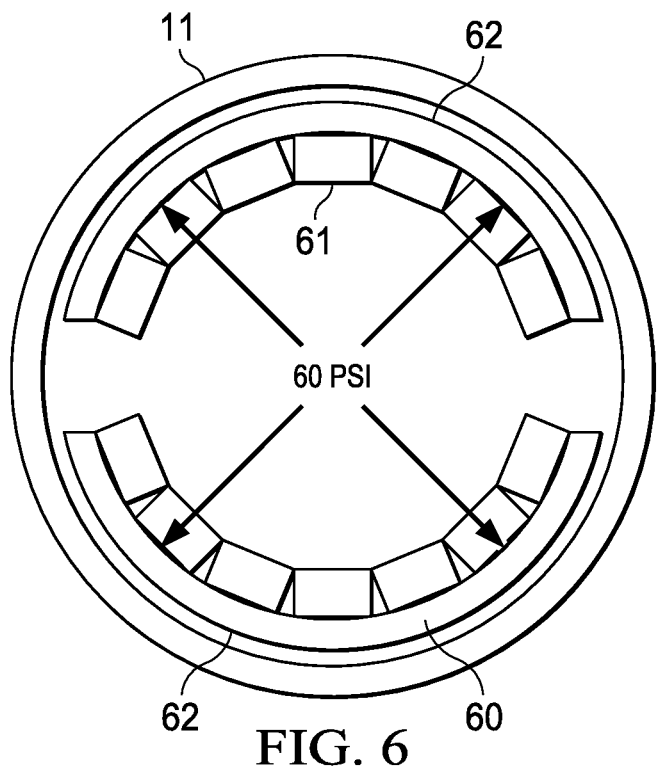

FIGS. 5 and 6 illustrate two MsS sensor configurations that have the ability to expand and contract. Either the sensor 50 of FIG. 5 or the sensor 60 of FIG. 6 could be used for sensor 31 of probe 30. The magnet portion 51 and 61 of each of these sensors is segmented into a ring of small magnets, which enhances flexibility of the sensor.

FIG. 5 illustrates a sensor 50, whose coil-wrapped strip 52 has one axial cut to allow for expansion. Strip 52 covers about all but a small gap of the tube inner diameter.

FIG. 6 illustrates a sensor 60 whose coil-wrapped strip 62 is split into two parts, with two small gaps separating them. Optionally, coil 62 can be split to a larger number of segments. These individual segments can be operated as a single coil if they are all connected in a sequence. Alternatively, the segments can be operated as a number of individually driven coils.

The term "ring-shaped" as used herein to describe the strip and magnet of the sensors is meant to encompass strips and magnets that have small gaps or are segmented as in FIGS. 5 and 6. Other means may be used for providing some radial flexibility to the sensors, such as the materials from which they are made. For example, segmented magnets may be attached to a flexible backing.

Although the expandable tip of probe 30 is designed to provide optimum coupling of sensors 31 to the inner wall of tube 11, the condition of the tube's inner diameter can be rough. This roughness might prevent the quality of coupling needed for the transmission and reception of guided waves.

Figure 7:
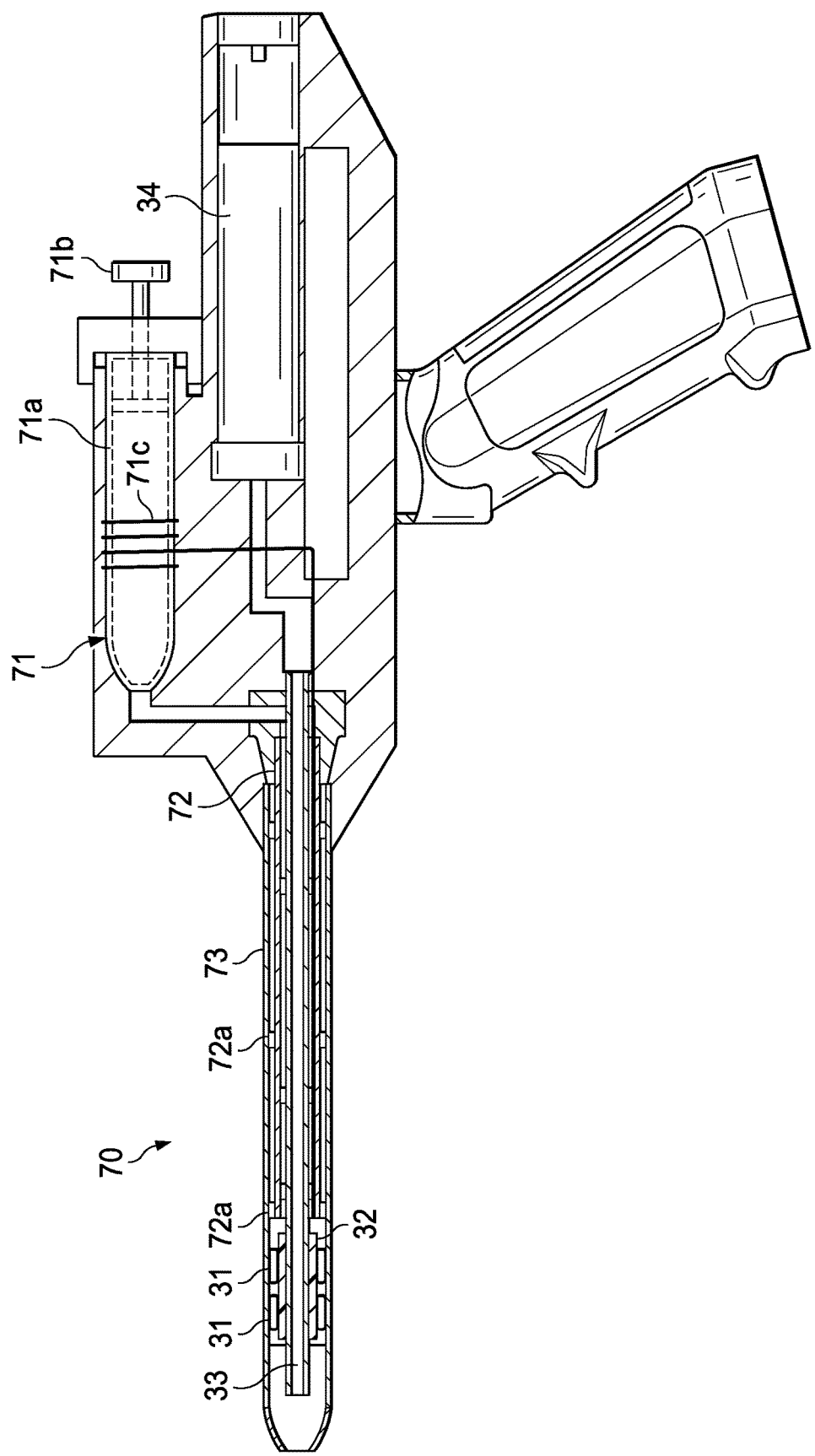
FIG. 7 illustrates a probe having an expandable probe head like that of FIG. 3, and also having a fluid couplant injector and associated structure.

FIG. 7 illustrates a probe 70 having the features of probe 30, but also having a fluid couplant injector 71 and associated structure. The features of probe 70 that are analogous to those of FIG. 3 have like reference numerals.

The couplant injector 71 delivers a fluid couplant to the probe head, via a couplant tube 72. Couplant injector comprises a couplant cartridge 71*a*, an injection mechanism 71*b*, and an optional heater 71*c*.

Referring to both FIGS. 3 and 7, the innermost tube of probe 70 is the bladder tube 33 that delivers pressurizing fluid to bladder 32. Bladder tube 33 extends to the most distal portion of probe 70 (the probe tip) when probe 70 is inserted into a tube 11 for testing.

In the embodiment of FIG. 7, sensors 31 are positioned over bladder 32 but inside outer tube 72. This is in contrast to the configuration of FIGS. 3 and 4, in which the sensors 31 are placed outside of outer tube 35. Both configurations are acceptable for either embodiment, but placing the sensors inside the outer tube will better protect the sensors. In both configurations, the sensors and tube are flexible as described above, to allow expansion in response to the expansion of bladder 32, thereby pressing sensors 31 toward the inner diameter of the tube under test.

Couplant tube 72 is also hollow, and has a slightly larger diameter than bladder tube 33. It is placed around bladder tube 33 but does not extend as far toward the probe tip. The portion of bladder tube 33 that extends past couplant tube 72 is the portion upon which bladder 32 and sensors 31 are attached as described above.

Couplant tube 72 has nozzles 72a in the area closest to the probe head. These nozzles 72a extend through outer tube 73 and disperse couplant through outer tube 73 and to and on the outer surface of the probe. The couplant fills gaps and voids between the probe head and the inner diameter of tube 11. Typically, the couplant is delivered before the probe head is mechanically pressurized (by activating bladder 32) against the tube's inner surface.

The couplant fluid is typically a high viscosity shear wave couplant. Because of the high viscosity of the couplant, the couplant injector 71 has a built-in heater 71c to facilitate removal of the probe out after MsS data acquisition. In the embodiment of FIG. 7, the heater is an electrical heating coil. Heating the couplant up to 150° F. is expected to sufficiently reduce the viscosity of the couplant. Although not shown in FIG. 7, a water rinse system can be incorporated in the probe head to remove (dissolve) the couplant.

An example of a suitable couplant is decomposed sugar. The percentage of water mixed with the sugar is in the range of 12-15%.

Figure 8:
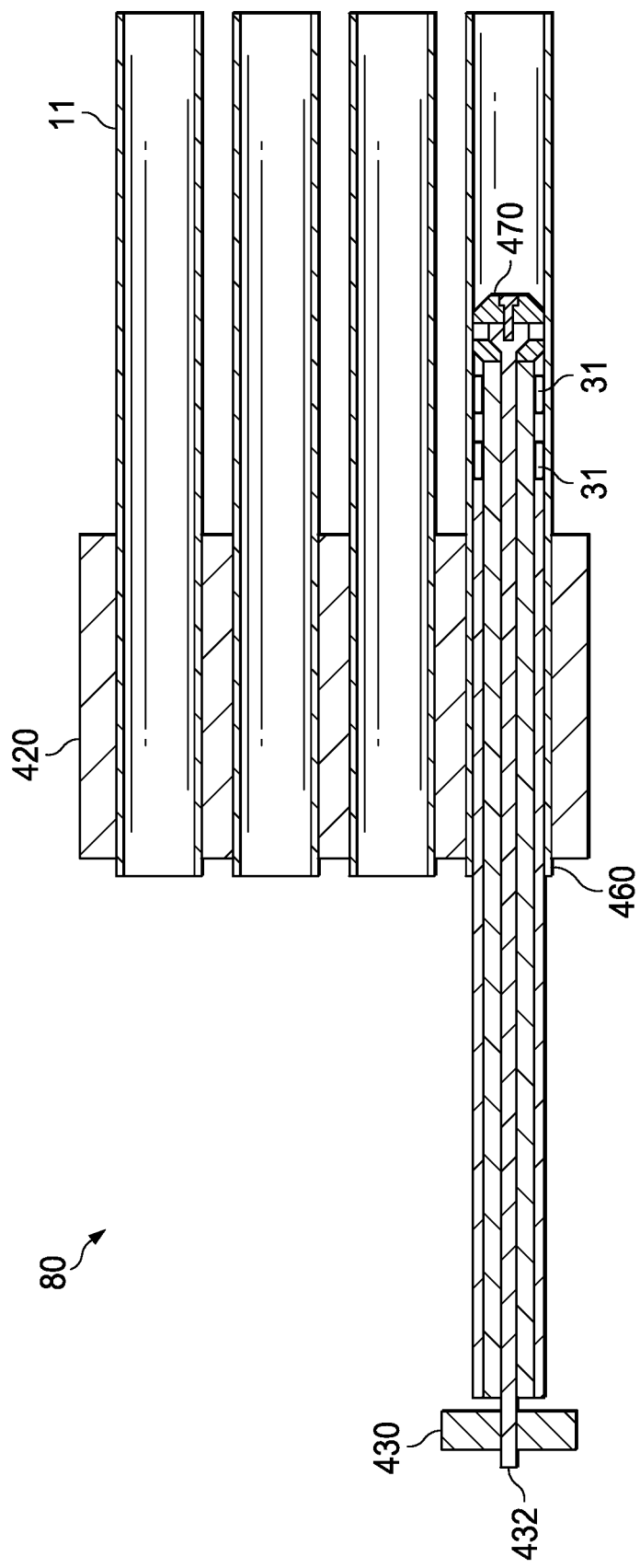
FIGS. 8 and 9 illustrate alternative mechanisms for expanding the probe head.
Figure 9:
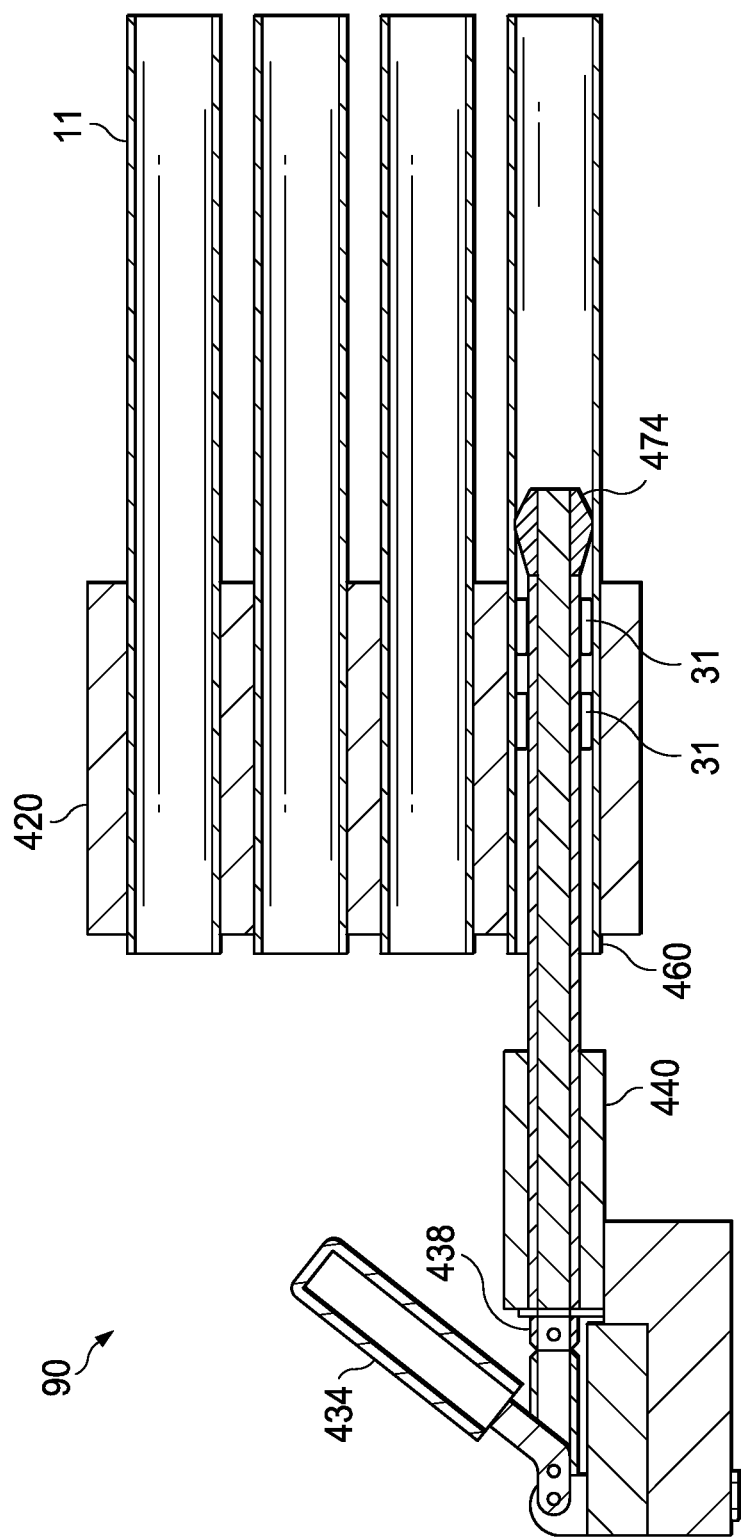

FIGS. 8 and 9 illustrate alternative mechanisms for expanding the probe head. These mechanisms may be used in place of a bladder and pressurizing cartridge to cause expansion of the outer tube 460 in the area of the probe head. In both FIGS. 8 and 9, the probe is shown inserted into a tube 11 of a heat exchanger having a tube sheet 420.

In FIG. 8, probe 80 has an expanding collet 470, activated by repositioning a drawbar 432. A nut 430 may be used to tighten the drawbar 432. In FIG. 9, probe 90 has a nosepiece 474 and drawbar 438. When the drawbar 438 is repositioned with handle 434, the nosepiece 474 is pulled into the flexible portion of the outer tube 460, causing that portion of the outer tube 460 to expand. Both mechanisms are further described in U.S. Pat. No. 7,019,520, entitled "Method and System for Torsional Wave Inspection of Heat Exchanger Tubes, to Kwun et al. and incorporated herein by reference.

In both embodiments of FIGS. 8 and 9, sensors 31 are placed immediately over or below the expanding surface of the outer tube 460 as described above.

Either of the expanding tip mechanisms of FIG. 8 or 9 may be used with the couplant injector of FIG. 7. The drawbars 432 or 438 would replace bladder tube 33, and the pressurization cartridge 34 would be replaced with the drawbar tightening mechanisms at the outside end of the probe.

What is claimed is:

1. A probe for use in magnetostrictive testing of a tubular structure, comprising:
    an outer tube having a probe head portion for insertion into the tubular structure, the outer tube being radially expandable at the probe head portion;
    a pair of magnetostrictive sensors in or on the probe head portion of the outer tube, each sensor comprising a ring-shaped magnet and a ring-shaped strip made from ferromagnetic material, the strip being concentric to and having a larger diameter than the magnet, the strip having an electrical coil wrapped around its width, and the magnet being polarized in a direction parallel to the longitudinal dimension of the outer tube;
    a flexible bladder located inside the outer tube in the area of the probe head;
    a probe handle attached to the outer tube at the end opposite the probe head;
    a pressurizing cartridge located in or on the probe handle, operable to store pressurizing fluid;
    a bladder tube extending longitudinally inside the outer tube, the bladder tube operable to deliver the pressurizing fluid from the pressurizing cartridge to the bladder, thereby causing the bladder to expand;
    a couplant cartridge located in or on the probe handle, operable to store couplant fluid;
    a couplant tube around and concentric to the bladder tube extending to the probe head, the couplant tube having nozzles for fluid communication of the couplant fluid out of the couplant tube;
    wherein the outer tube has openings operable to communicate the couplant fluid from the couplant tube toward the inner surface of the tubular structure.

2. The probe of claim 1, wherein the magnet is segmented into a series of small magnets.

3. The probe of claim 1, further comprising a heater located on the probe head for heating the couplant fluid.

4. The probe of claim 1, wherein the sensors are separated along the longitudinal dimension of the outer tube by 0.25 wavelength.

5. The probe of claim 1, wherein the sensors are radially expandable.

6. The probe of claim 5, wherein each sensor is radially expandable by means of one or more gaps in the strip and the magnet.

7. A probe for use in magnetostrictive testing of a tubular structure, comprising:
    an outer tube having a probe head portion for insertion into the tubular structure, the outer tube being radially expandable at the probe head portion;
    a pair of magnetostrictive sensors in or on the probe head portion, each sensor comprising a ring-shaped magnet and a ring-shaped strip made from ferromagnetic material, the strip being concentric to and having a larger diameter than the magnet, the strip having an electrical coil wrapped around its width, and the magnet being polarized in a direction parallel to the longitudinal dimension of the outer tube;
    an expansion mechanism operable to expand the probe head portion of the outer tube;
    a probe handle attached to the outer tube at the end opposite the probe head;
    a couplant cartridge located in or on the probe handle, operable to store couplant fluid;
    a couplant tube inside of and concentric to the outer tube, and extending to the probe head, and having nozzles for fluid communication of the couplant fluid out of the couplant tube;
    wherein the outer tube has openings operable to communicate the couplant fluid from the couplant tube toward the inner surface of the tubular structure.

8. The probe of claim 7, wherein the expansion mechanism is an expanding collet, a variable diameter nosepiece, or an expanding bladder.

9. The probe of claim 7, wherein the magnet is segmented into a series of small magnets.

10. The probe of claim 7, further comprising a heater located on the probe head for heating the couplant fluid.

11. The probe of claim 7, wherein the sensors are separated along the longitudinal dimension of the outer tube by 0.25 wavelength.

12. The probe of claim 7, wherein the sensors are radially expandable.

13. The probe of claim 12, wherein each sensor is radially expandable by means of one or more gaps in the strip and the magnet.

14. A method of using a magnetostrictive probe for testing of a tubular structure, comprising:

inserting a probe head portion of the probe into an open end of the tubular structure;

wherein the probe has an outer tube that is radially expandable at the probe head portion, and a pair of magnetostrictive sensors in or on the probe head portion, each sensor comprising a ring-shaped magnet and a ring-shaped strip made from ferromagnetic material, the strip being concentric to and having a larger diameter than the magnet, the strip having an electrical coil wrapped around its width, and the magnet being polarized in a direction parallel to the longitudinal dimension of the outer tube;

delivering fluid couplant toward the probe head via a couplant tube extending to but not past the probe head, the couplant tube having nozzles for fluid communication of the couplant fluid out of the couplant tube;

wherein the outer tube has openings operable to communicate the couplant fluid from the couplant tube to the outer surface of the outer tube;

expanding the probe head such that the sensors move toward the inner diameter of the tubular structure;

applying an AC current to the sensor;

wherein the sensors are operable to generate waves within the tubular structure and to respond to waves reflected from aberrations in the tubular structure.

15. The method of claim 14, wherein the expanding step is performed by inflating a bladder inside the probe head.

16. The method of claim 14, wherein the expanding step is performed by enlarging a collet located in the probe head.

17. The method of claim 14, wherein the expanding step is performed by drawing a variable diameter nosepiece into an open end of the outer tube.

* * * * *